US00PP30467P2

(12) United States Plant Patent
Koot

(10) Patent No.: US PP30,467 P2
(45) Date of Patent: Apr. 30, 2019

(54) ***BIDENS* PLANT NAMED 'DOBIBITORA'**

(50) Latin Name: *Bidens ferulifolia*
Varietal Denomination: Dobibitora

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,738

(22) Filed: Dec. 21, 2017

(51) Int. Cl.
*A01H 5/02* (2018.01)

(52) U.S. Cl.
USPC ..... Plt./410

(58) Field of Classification Search
USPC ..... Plt./410
See application file for complete search history.

*Primary Examiner* — Susan McCormick Ewoldt
(74) *Attorney, Agent, or Firm* — C. A. Whealy

(57) ABSTRACT

A new and distinct cultivar of *Bidens* plant named 'Dobibitora', characterized by its compact, semi-upright to trailing and mounding plant habit; moderately vigorous growth habit; freely branching habit; early and freely flowering habit; large inflorescences with bright yellow, yellow orange and orange-colored ray florets and yellow to yellow orange-colored disc florets; and strong and flexible peduncles that hold the inflorescences above and beyond the foliar plane.

1 Drawing Sheet

Botanical designation: *Bidens ferulifolia.*
Cultivar denomination: 'DOBIBITORA'.

BACKGROUND OF THE INVENTION

The present invention relates to a new and distinct cultivar of *Bidens* plant, botanically known as *Bidens ferulifolia* and hereinafter referred to by the name 'Dobibitora'.

The new *Bidens* plant is a product of a planned breeding program conducted by the Inventor in Rheinberg, Germany. The objective of the breeding program is to create new compact and early-flowering *Bidens* plants with numerous large and attractive inflorescences.

The new *Bidens* plant originated from a cross-pollination made by the Inventor in Rheinberg, Germany in July, 2015 of a proprietary selection of *Bidens ferulifolia* identified as code number BB14-001214-002, not patented, as the female, or seed, parent with a proprietary selection of *Bidens ferulifolia* identified as code number BB14-001114-003, not patented, as the male, or pollen, parent. The new *Bidens* plant was discovered and selected by the Inventor as a single flowering plant from within the progeny of the stated cross-pollination in a controlled greenhouse environment in Rheinberg, Germany in May, 2017.

Asexual reproduction of the new *Bidens* plant by vegetative terminal cuttings in a controlled greenhouse environment in Rheinberg, Germany since June, 2017 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dobibitora'. These characteristics in combination distinguish 'Dobibitora' as a new and distinct *Bidens* plant:

1. Compact, semi-upright to trailing and mounding plant habit.
2. Moderately vigorous growth habit.
3. Freely branching habit.
4. Early and freely flowering habit.
5. Large inflorescences with bright yellow, yellow orange and orange-colored ray florets and yellow to yellow orange-colored disc florets.
6. Strong and flexible peduncles that hold the inflorescences above and beyond the foliar plane.

Plants of the new *Bidens* differ primarily from plants of the female parent selection in the following characteristics:

1. Plants of the new *Bidens* are more compact than plants of the female parent selection.
2. Plants of the new *Bidens* have larger inflorescences than plants of the female parent selection.

Plants of the new *Bidens* differ primarily from plants of the male parent selection in the following characteristics:

1. Plants of the new *Bidens* are more compact than plants of the male parent selection.
2. Plants of the new *Bidens* have broader leaves than plants of the male parent selection.
3. Plants of the new *Bidens* flower earlier than plants of the male parent selection.

Plants of the new *Bidens* can be compared to plants of *Bidens triplinervia* 'Florbikano', disclosed in U.S. Plant Pat. No. 25,087. In side-by-side comparisons, plants of the new *Bidens* differ from plants of 'Florbikano' in the following characteristics:

1. Plants of the new *Bidens* are more compact than and not as vigorous as plants of 'Florbikano'.
2. Plants of the new *Bidens* have broader leaves than plants of 'Florbikano'.

3. Plants of the new *Bidens* flower earlier than plants of 'Florbikano'.
4. Plants of the new *Bidens* are more freely flowering than plants of 'Florbikano'.
5. Plants of the new *Bidens* and 'Florbikano' differ in ray and disc floret color as plants of 'Florbikano' have yellow orange and dark orange bi-colored ray florets and bright yellow-colored disc florets.

BRIEF DESCRIPTION OF THE PHOTOGRAPH

The accompanying photograph illustrates the overall appearance of the new *Bidens* plant showing the colors as true as it is reasonably possible to obtain in colored reproductions of this type. Colors in the photograph may differ slightly from the color values cited in the detailed botanical description which accurately describe the colors of the new *Bidens* plant. The photograph comprises a side perspective view of a typical flowering plant of 'Dobibitora' grown in a container.

DETAILED BOTANICAL DESCRIPTION

The aforementioned photograph and following observations and measurements describe plants grown in 22-cm containers during the spring and early summer in a glass-covered greenhouse in Rheinberg, Germany and under cultural practices typical of commercial *Bidens* production. During the production of the plants, day and night temperatures averaged 18° C. and light levels averaged 4,500 lux. Plants were 13 weeks old when the photograph and description were taken. In the following description, color references are made to The Royal Horticultural Society Colour Chart, 2007 Edition, except where general terms of ordinary dictionary significance are used.

Botanical classification: *Bidens ferulifolia* 'Dobibitora'.

Parentage:

*Female parent*.—Proprietary selection of *Bidens ferulifolia* identified as code number BB14-001214-002, not patented.

*Male parent*.—Proprietary selection of *Bidens ferulifolia* identified as code number BB14-001114-003, not patented.

Propagation:

*Type*.—By terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; color, close to 155B.

*Rooting habit*.—Freely branching; moderately dense.

Plant description:

*Plant and growth habit*.—Compact, semi-upright to trailing and mounding plant habit; moderately vigorous growth habit.

*Branching habit*.—Freely branching habit with about 23 primary lateral branches each with about six to eight secondary lateral branches.

*Plant height, soil level to top of foliar plane*.—About 31.5 cm.

*Plant height, soil level to top of floral plane*.—About 32 cm.

*Plant diameter or spread*.—About 72 cm.

*Lateral branches*.—Length: About 39 cm. Diameter: About 4 mm. Internode length: About 5 cm. Strength: Strong. Texture and luster: Pubescent; semi-glossy. Color, developing: Close to 144C. Color, fully developed: Close to 146B.

Leaf description:

*Arrangement*.—Opposite, simple or trifoliate.

*Leaf length*.—About 4 cm.

*Leaf width*.—About 3.2 cm.

*Leaflet length*.—About 1.8 to 3 cm.

*Leaflet width*.—About 9 mm to 15 mm.

*Shape*.—Trullate.

*Apex*.—Apiculate.

*Base*.—Acute.

*Margin*.—Moderately incised; laciniate; sinuses divergent.

*Texture and luster, upper and lower surfaces*.—Smooth, glabrous; matte.

*Venation pattern*.—Pinnate.

*Color*.—Developing leaves, upper surface: Close to N137B. Developing leaves, lower surface: Close to 137B. Fully expanded leaves, upper surface: Close to 137B; venation, close to 137B; color does not change in the autumn. Fully expanded leaves, lower surface: Close to 148B; venation, close to 138B; color does not change in the autumn.

*Petioles*.—Length: About 1.2 cm. Diameter: About 1.2 mm. Strength: Moderately strong. Texture and luster, upper and lower surfaces: Smooth, glabrous; semi-glossy. Color, upper and lower surfaces: Close to 146C.

Inflorescence description:

*Appearance*.—Single (daisy) inflorescence form with ray and disc florets forming acropetally on a receptacle; inflorescences positioned above and beyond the foliar plane on strong and flexible peduncles; inflorescences face upright to outwardly.

*Flowering habit*.—Freely flowering habit; about 275 to 325 inflorescences developing per plant during the flowering season.

*Fragrance*.—None detected.

*Natural flowering season*.—Plants flower continuously during the spring in Germany; early flowering habit, plants begin flowering about five weeks after planting.

*Inflorescence longevity*.—Individual inflorescences last about one week on the plant; inflorescences persistent.

*Inflorescence buds*.—Height: About 1.2 cm. Diameter: About 5 mm. Shape: Oblong. Texture and luster: Rippled; semi-glossy. Color: Close to 144B.

*Inflorescence size*.—Diameter: About 3.2 cm. Depth (height): About 8 mm. Disc diameter: About 7 mm. Receptacle diameter: About 4 mm. Receptacle height: About 4.5 mm. Receptacle color: Close to 7A and 144C.

*Ray florets*.—Number of ray florets per inflorescence: About five to eight arranged in a single whorl. Length: About 1.4 cm. Width: About 8 mm. Shape: Elliptical to ovate. Apex: Emarginate. Base: Obtuse. Margin: Entire. Texture and luster, upper and lower surfaces: Smooth, glabrous; matte. Color: When opening, upper surface: Close to 17A, 8A and 45A. When opening, lower surface: Close to 15A. Fully opened, upper surface: Close to 17A, 8A and N25A; venation, close to 164B; color does not change with development. Fully opened, lower surface: Close to 13A; venation, close to 164B; color does not change with development.

*Disc florets*.—Number of disc florets per inflorescence: About 50 arranged in about three to four whorls. Shape: Tubular, elongated; apex, five-pointed. Length: About 5.2 mm. Diameter: About 1 mm. Texture and luster, inner and outer surfaces: Smooth, glabrous; matte. Color, when opening, inner and outer surfaces: Close to 7A. Color, fully opened, inner and outer surfaces: Close to 14A.

*Phyllaries*.—Quantity per inflorescence: About six to eight in a single whorl. Length: About 5 mm. Width: About 1 mm. Shape: Elliptical, elongated. Apex: Acute. Base: Truncate. Margin: Entire. Texture and luster, upper and lower surfaces: Smooth, glabrous; matte. Color, upper and lower surfaces: Close to 144B.

*Peduncles*.—Length, terminal peduncle: About 5 cm. Diameter, terminal peduncle: About 1.5 mm. Length, third peduncle: About 4 cm. Diameter, third peduncle: About 1.2 mm. Strength: Strong; flexible. Aspect: Upright to outwardly, inflorescences held above and beyond the foliar plane. Texture and luster: Smooth, glabrous; semi-glossy. Color: Close to 146A.

*Reproductive organs*.—Androecium: Present on disc florets only. Quantity per disc floret: Two. Filament length: About 2 mm. Filament color: Close to 7A. Anther shape: Oval. Anther size: About 1 mm by 3 mm. Anther color: Close to 202A. Pollen amount: Scarce. Pollen color: Close to 14A. Gynoecium: Present disc florets only. Quantity per disc floret: One. Pistil length: About 7 mm. Style length: About 4 mm. Style color: Close to 9C. Stigma diameter: About 2 mm. Stigma shape: Bifurcate. Stigma color: Close to 15A. Ovary color: Close to 145C.

*Fruits and seeds*.—Fruit and seed development has not been observed on plants of the new *Bidens* to date.

Pathogen & pest resistance: Plants of the new *Bidens* have not been shown to be resistant to pathogens and pests common to *Bidens* plants to date.

Garden performance: Plants of the new *Bidens* have exhibited good tolerance to rain and wind and have been observed to tolerate temperatures from about 3° C. to about 28° C. and to be suitable for USDA Hardiness Zone 11.

It is claimed:

1. A new and distinct *Bidens* plant named 'Dobibitora' as illustrated and described.

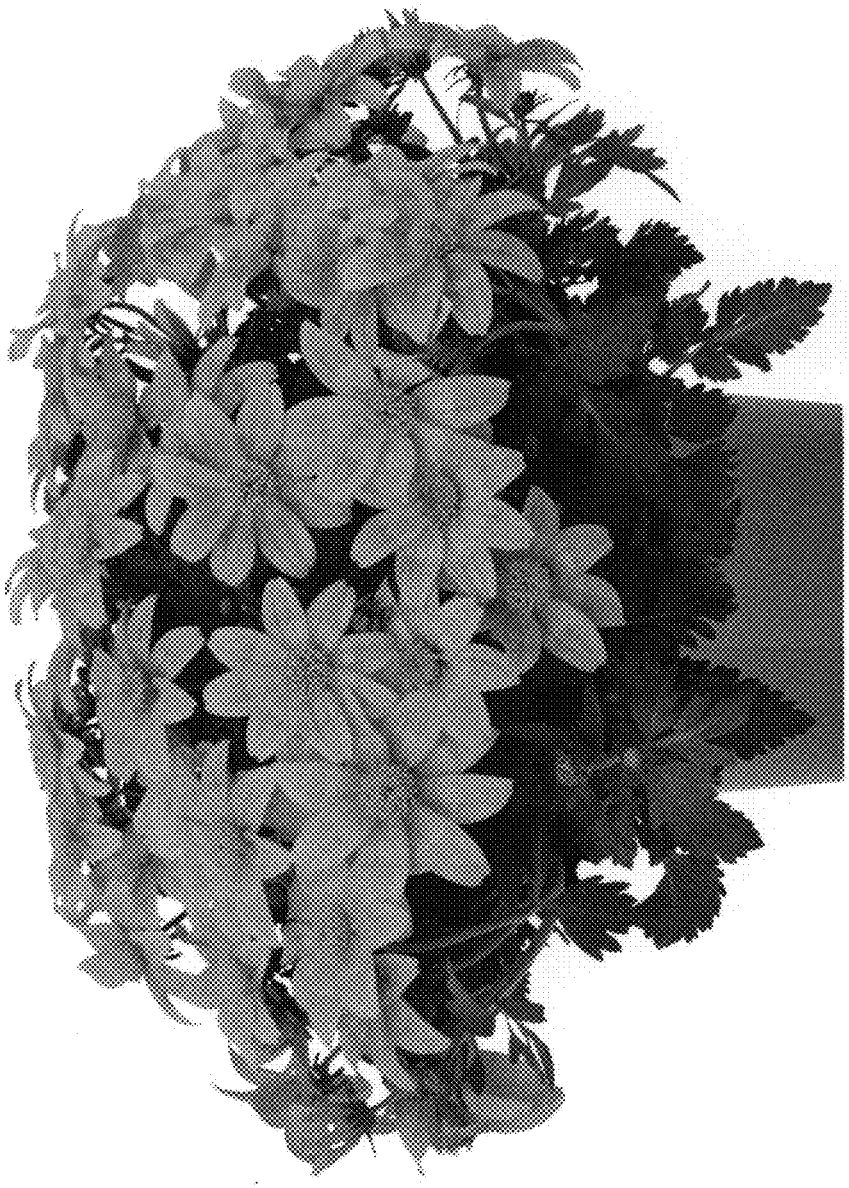

* * * * *